United States Patent
Garcia et al.

(10) Patent No.: US 11,246,867 B2
(45) Date of Patent: Feb. 15, 2022

(54) PHARMACEUTICAL COMPOSITION COMPRISING PIMOBENDAN

(71) Applicant: Ceva Sante Animale, Libourne (FR)

(72) Inventors: Rosita Garcia, Laval (FR); Romain Charles, Laval (FR)

(73) Assignee: Ceva Sante Animale, Libourne (FR)

(*) Notice: Subject to any disclaimer, the term of this patent is extended or adjusted under 35 U.S.C. 154(b) by 488 days.

(21) Appl. No.: 16/061,623

(22) PCT Filed: Dec. 16, 2016

(86) PCT No.: PCT/EP2016/081364
§ 371 (c)(1),
(2) Date: Jun. 12, 2018

(87) PCT Pub. No.: WO2017/103054
PCT Pub. Date: Jun. 22, 2017

(65) Prior Publication Data
US 2020/0261451 A1    Aug. 20, 2020

(30) Foreign Application Priority Data
Dec. 17, 2015  (EP) .................................... 15307048

(51) Int. Cl.
| | | |
|---|---|---|
| *A61K 31/501* | (2006.01) | |
| *A61K 9/16* | (2006.01) | |
| *A61K 47/02* | (2006.01) | |
| *A61K 47/12* | (2006.01) | |
| *A61K 47/26* | (2006.01) | |
| *A61K 47/36* | (2006.01) | |
| *A61K 47/38* | (2006.01) | |

(52) U.S. Cl.
CPC .......... *A61K 31/501* (2013.01); *A61K 9/1694* (2013.01); *A61K 47/02* (2013.01); *A61K 47/12* (2013.01); *A61K 47/26* (2013.01); *A61K 47/36* (2013.01); *A61K 47/38* (2013.01)

(58) Field of Classification Search
CPC ...... A61K 31/501; A61K 47/02; A61K 47/12; A61K 47/26; A61K 47/36; A61K 47/38; A61K 9/1694; A61K 9/2013
See application file for complete search history.

(56) References Cited

U.S. PATENT DOCUMENTS

| | | | |
|---|---|---|---|
| 8,846,680 B2 * | 9/2014 | Folger | A61K 9/2009 |
| | | | 514/252.06 |
| 10,398,705 B2 * | 9/2019 | Folger | A61K 31/501 |
| 2005/0203097 A1 * | 9/2005 | Folger | A61K 47/46 |
| | | | 514/252.06 |

FOREIGN PATENT DOCUMENTS

| | | |
|---|---|---|
| EP | 1725218 | 6/2014 |
| WO | 2010/055119 | 5/2010 |
| WO | 2013/135852 | 9/2013 |

OTHER PUBLICATIONS

PetCoach article (Year: 2020).*
Vetmedin (Freedom of Information Summary, NADA 141-273 Boehringer Ingelheim, Apr. 30, 2007). (Year: 2007).*
International Search Report and Written Opinion corresponding to International Patent Application No. PCT/EP2016/081364 dated Mar. 8, 2017; 12 pages.

* cited by examiner

*Primary Examiner* — Umamaheswari Ramachandran
(74) *Attorney, Agent, or Firm* — Leason Ellis LLP

(57) ABSTRACT

The invention relates to oral pharmaceutical compositions comprising pimobendan pharmaceutically active compound. It also relates to a method for preparing the same uses thereof.

10 Claims, 4 Drawing Sheets

PHARMACEUTICAL COMPOSITION COMPRISING PIMOBENDAN

TECHNICAL FIELD

The invention relates to the field of animal health. In particular, the invention relates to novel oral pharmaceutical compositions comprising pimobendan as pharmaceutically active compound.

BACKGROUND INFORMATION

Pimobendan (4,5-dihydro-6-[2-(4-methoxyphenyl)-1H-benzimidazol-5-yl]-5-methyl-3(2H)-pyridazone) is disclosed in EP 0008391 B1. Pimobendan is a cardiotonic, hypotensive and anti-thrombotic. Said substance is the standard in the indication of congestive heart failure.

Pimobendan is characterized by a low solubility in aqueous media and a very highly pH-dependent solubility. EP 0439030 discloses the low solubility of pimobendan in aqueous environment which is still characterized by a highly pH-dependent nature. Depending on the buffer system used, about 100 to 300 mg/liter dissolve at a pH between 1 and 3, but at pH 5 only about 1 mg/liter will dissolve in water. In humans, this phenomenon resulted in strongly fluctuating blood concentrations that levels were often too low. These unsatisfactory absorption characteristics were explained by the high pH-dependency of the solubility of pimobendan in aqueous media and by fluctuating pH conditions in the gastrointestinal tract of the test subjects. According to this patent, the low solubility and high pH dependency of the solubility of pimobendan can be overcome by using an intimate dry admixture of powdered pimobendan and powdered citric acid wherein said admixture is up to about one part by weight of pimobendan per no less than about five parts by weight of citric acid and pharmaceutically active carriers, being filled into capsules or compressed into tablets for oral administration. The strongly fluctuating blood concentrations are said to be prevented by the acid microsphere, which is caused by the dissolving rate of citric acid, formed around the pimobendan particles. Said microsphere is always acidic and ensures a reliable, practically pH-independent dissolution and absorption of pimobendan.

According to EP 1725218 B1, the high quantity of citric acid and its acidic taste is not readily accepted by most animals. Thus, these formulations have to be force-fed to the animals or mixed with food prior to application, these difficulties can be overcome by using a formulation preferably in the form of tablets. In that context, EP 1725218 B1 relates to a novel solid formulation comprising pimobendan which is homogeneously dispersed in a polyvalent acid selected from the group consisting of citric acid, acetic acid, tartaric acid or its anhydride, and a flavouring substance. According to EP1725218B, to formulate a voluntarily accepted, long-term stable, large scale producible, homogenously dispersed, fast-releasing solid formulation, a process was invented where fluid-bed granulation process was carried out. Most preferred is a tablet characterized in that the tablet comprises 1.25 mg, 2.5 mg, 5 mg or 10 mg pimobendan, and further comprises citric acid, preferably at an amount of 50 mg/g of the solid formulation, artificial beef flavour and pharmaceutically acceptable excipients. However, said tablets present a large size and hardness thereof is quite high so that some small animals spit them out.

WO 2010/055119 discloses a formulation, comprising pimobendan and an organic carboxylic acid, wherein the only organic carboxylic acid is succinic acid, and the weight ratio of succinic acid to pimobendan is at least 11:1. WO 2010/010257 relates to the use of a coating composition for application to a solid veterinary pharmaceutical composition made from pimobendan by a method of film coating comprising a powder appetizing material, a binder and a solvent. The method for preparing such formulations can thus be difficult and expensive.

The problem underlying the present invention was to provide pimobendan solid formulations of medium sizes and with still an effective amount of pimobendan and a diminished hardness so that feeding and/or swallowing thereof are rendered easier to mammalian subjects, especially small animals, allowing thereby a good compliance of the treatment.

BRIEF SUMMARY OF THE INVENTION

The invention relates to novel solid formulations comprising, more particularly as pharmaceutically active compound, pimobendan or a pharmaceutically acceptable salt thereof which is dispersed, preferably homogenously dispersed, in malic acid and a flavor acceptable to small animals. Preferably, such solid formulations are granules or tablets. Most preferred is a tablet characterized in that the tablet comprises, preferably consists of, 1.25 mg, 2.5 mg, 5 mg or 10 mg pimobendan, and further consists of lactose, corn starch, microcrystalline cellulose, croscarmellose-sodium (crosslinked sodium carboxymethyl cellulose), malic acid, preferably at an amount of 100 mg/1.5 g of the solid formulation, pig liver flavor, copovidone (copolymer of polyvinyl pyrrolidone and polyvinyl acetate), colloidal anhydrous silica and stearic acid.

The solid formulations according to the invention are prepared by wet granulation, optionally followed by compression the granules into tablets. In the preferred embodiment purified water is used as granulation liquid.

The invention also relates to a process for preparation of the solid formulations comprising the following steps:
a) mixing pimobendan or a pharmaceutically acceptable salt thereof or crystalline forms thereof, a first part of a disintegrant (e.g. croscarmellose), malic acid, at least one diluent (such as starch, lactose and/or cellulose derivatives), a flavoring agent (e.g. pig liver flavor, yeast), optionally at least one glidant (e.g. colloidal silicone dioxide),
b) wet granulating the blend obtained in step a) with at least one binder (such as copovidone) and water,
c) drying the obtained granules and optionally milling,
d) mixing the dried granules obtained in step c) with a second part of the disintegrant (e.g. croscarmellose),
e) mixing at least one lubricant (e.g. stearic acid), and at least one glidant (e.g. anhydrous colloidal silica) to the granules obtained in step d),
and f) optionally compressing the mixture obtained in step d) to form a tablet.

Step f) is omitted if the solid formulation corresponds to granules. If the solid formulation is a tablet, step f) is carried out.

Furthermore, the invention relates to a method of prevention and/or treatment of diseases wherein cardiotonic, hypotensive and anti-thrombotic substances have a therapeutic benefit, comprising administering to a mammal in need of such treatment a therapeutically effective amount of a solid formulation according to the invention as disclosed above.

Preferred is a method of prevention and/or treatment of congestive heart failure, comprising administering to a mammal in need of such treatment a therapeutically effective amount of a solid formulation according to the invention as disclosed above. Most preferably, the method comprises administering a tablet according to the invention, as defined above.

Furthermore, the invention relates to a method for manufacturing a medicament for the prevention and/or treatment of congestive heart failure, characterized in that a solid formulation according to the invention is used. Preferably, the invention relates to a method for manufacturing a medicament for the prevention and/or treatment of congestive heart failure, characterized in that a tablet comprising, preferably consisting of 1.25 mg, 2.5 mg, 5 mg or 10 mg pimobendan and further consisting of lactose, corn starch, microcrystalline cellulose, croscarmellose-sodium, malic acid, pig liver flavor, copovidone, colloidal anhydrous silica and stearic acid is used.

DETAILED DESCRIPTION OF THE INVENTION

Figure 1:
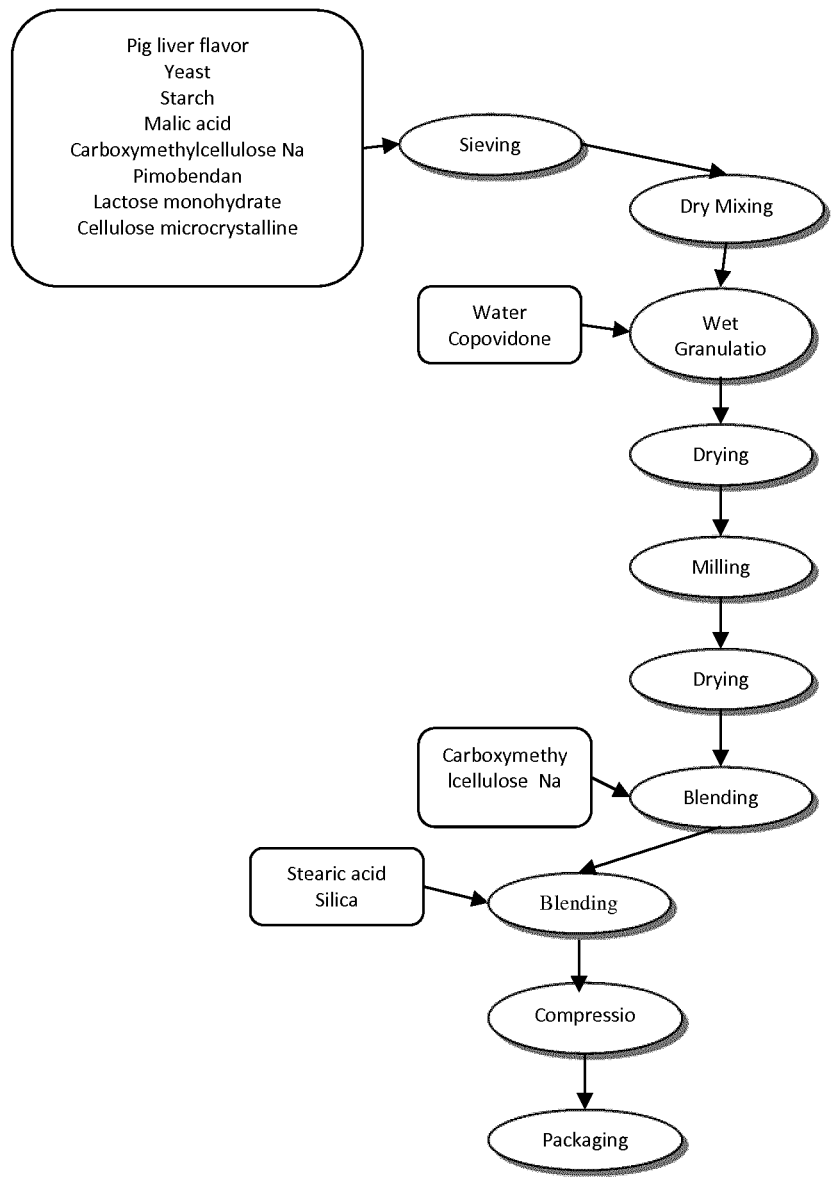
FIG. 1: Flow chart of a manufacturing process according to the invention

Before the embodiments of the present invention it must be noted that as used herein and in the appended claims, the singular forms "a", "an", and "the" include plural reference unless the context clearly dictates otherwise. Thus, for example, reference to "a tablet" includes a plurality of such tablets, reference to the "carrier" is a reference to one or more carriers and equivalents thereof known to those skilled in the art, and so forth. Unless defined otherwise, all technical and scientific terms used herein have the same meanings as commonly understood by one of ordinary skill in the art to which this invention belongs. All given ranges and values may vary by 1% to 5% unless indicated otherwise or known otherwise by the person skilled in the art, therefore, the term "about" was omitted from the description. Although any methods and materials similar or equivalent to those described herein can be used in the practice or testing of the present invention, the preferred methods, devices, and materials are now described.

All publications mentioned herein are incorporated herein by reference for the purpose of describing and disclosing the substances, excipients, carriers, and methodologies as reported in the publications which might be used in connection with the invention.

The solution to the above technical problem is achieved by the description and the embodiments characterized in the claims.

With the wet-granulation process according to the invention, Pimobendan was homogenously dispersed. Such solid formulations comprising a flavor suitable for small animals and malic acid allows a formulation comprising malic acid with a satisfactory palatability. Solid formulations of the invention do not have to be force-fed to the animals or mixed with food prior to application.

In a first embodiment, the invention relates to a solid formulation, comprising pimobendan or a pharmaceutically acceptable salt thereof, which is dispersed, advantageously homogenously dispersed, in malic acid and a flavor acceptable to small animals.

Such flavors according to the invention preferably are selected from artificial beef flavors, artificial chicken flavors, pork (or pig) liver flavor (powder), natural or artificial meat flavor, yeast, yeast extract, honey flavor, and the like. Said flavors disguise the taste of the malic acid and of pimobendan.

Preferably, malic acid is anhydrous.

Preferably, the solid formulation according to the invention is a tablet or granule formulation. The granule formulation according to the invention is explained in more detail below. More preferably, the solid formulation is chewable.

The invention preferably also relates to a solid formulation according to the invention, further comprising one or several pharmaceutically acceptable excipients. Excipients according to the invention are preferably selected from the group consisting of diluents, disintegrants, carriers, binders, glidants, lubricants, solvents, and a mixture thereof. Any other excipients known to the skilled person and found suitable for the solid formulation according to the invention may also be comprised in the solid formulation according to the invention. See also Remington, J.P. The Science and Practice of Pharmacy (2013), 22th ed., London, Pharmaceutical Press.

More preferably, said excipients are carriers/diluents selected from the group lactose, starch, cellulose, microcrystalline cellulose and cellulose derivatives, e.g. methylcellulose, and the like. Any other carrier known to the skilled person and found suitable for the solid formulation according to the invention may also be comprised in the solid formulation according to the invention. See also Remington, J.P. The Science and Practice of Pharmacy (2013), 22th ed., London, Pharmaceutical Press.

According to a particular embodiment, the solid formulation further comprises microcrystalline cellulose. In this particular embodiment, the solid formulation is a granule formulation or preferably is in tablet form.

One or several binders according to the invention are preferably selected from the group consisting of polyvidone (used synonymously for povidone or polyvinyl pyrrolidone), copovidone (copolymer of polyvinyl pyrrolidone and polyvinyl acetate), methylcellulose, hydroxypropylmethylcellulose (HPMC), hydroxymethylcellulose, starch, gelatine, and the like. Any other binder known to the skilled person and found suitable for the solid formulation according to the invention may also be comprised in the solid formulation according to the invention. See also Remington, J.P. The Science and Practice of Pharmacy (2013), 22th ed., London, Pharmaceutical Press.

According to a particular embodiment, the solid formulation according to the invention further comprises povidone or copovidone, preferably copovidone.

The solid formulation according to the invention may also comprise one or several flow regulators or glidants selected from the group consisting of silica, preferably colloidal anhydrous silica, calcium silicate, magnesium silicate, talc, and the like. Any other flow regulator known to the skilled person and found suitable for the solid formulation according to the invention may also be comprised in the solid formulation according to the invention. See also Remington, J.P. The science and Practice of Pharmacy (loc. cit.).

The solid formulation according to the invention may also comprise one or several disintegrants selected from the group consisting of croscarmellose sodium, sodium starch glycolate, pregelatinised starch, cross-linked polyvinylpyrrolidone and the like. Any other disintegrant known to the skilled person and found suitable for the solid formulation according to the invention may also be comprised in the solid formulation according to the invention. See also Remington, J.P. The science and Practice of Pharmacy (loc. cit).

The solid formulation according to the invention may also comprise one or several lubricants selected from the group consisting of magnesium stearate, calcium stearate, glyceryl behenate, polyethylene glycol, stearic acid, talc and the like. Any other lubricant known to the skilled person and found suitable for the solid formulation according to the invention may also be comprised in the solid formulation according to the invention. See also Remington, J.P. The science and Practice of Pharmacy (loc. cit). The invention preferably also relates to a solid formulation according to the invention, wherein the carriers are starch and lactose. The invention preferably also relates to a solid formulation according to the invention, characterized in that the lactose consists of coarse particles greater than 200 μm in size. The person skilled in the art knows other types of lactose which are suitable as well as carrier according to the invention, e.g. fine lactose equal or smaller than 200 μm in size or spray-dried lactose. Preferred is lactose consisting of coarse particles greater than 200 μm in size.

According to a particular embodiment, the solid formulation according to the invention, preferably in tablet form, further comprises stearic acid (as a lubricant).

The invention preferably also relates to a solid formulation according to the invention, characterized in that the starch or various starches are selected from the group consisting of native starch, gelatinized starch, partly gelatinized starch, starch powder, starch granules, chemically modified starch and swellable physically modified starch.

The invention preferably also relates to a solid formulation according to the invention, characterized in that the starch is corn starch.

The invention preferably also relates to a solid formulation according to the invention, comprising 0.5 to 20 mg of pimobendan. The more preferred solid formulation contains 1 to 10 mg of pimobendan. The even more preferred solid formulation contains 1.25 to 10 mg of pimobendan. Most preferred solid formulations contain 1.25 mg, 2.5 mg, 5 mg or 10 mg of pimobendan.

The invention preferably also relates to a solid formulation according to the invention, comprising a content by weight of 1:10-1:40 of pimobendan in relation to malic acid anhydrous, preferably 1:20.

The invention preferably also relates to a solid formulation according to the invention, characterized in that the weight of the whole solid formulation is in the range of 250 to 3000 mg, with a more preferred weight range of 300 mg to 3000 mg, and most preferred weight of 375 mg, 1500 mg or 3000 mg. As mentioned before, the invention is advantageous in that the amount of pimobendan can be high compared to the size of the solid formulation, for instance the invention can provide tablets of 375 mg and contain 1.25 mg pimobendan, without impairing the taste or hardness of the tablets.

The invention preferably also relates to a solid formulation according to the invention, wherein the solid formulation is produced by a wet granulation process comprising or consisting of the steps:

a) mixing pimobendan or a pharmaceutically acceptable salt thereof or crystalline forms thereof, the first part of a disintegrant (e.g. croscarmellose), malic acid, at least one diluent (such as starch, lactose and/or cellulose derivatives), a flavoring agent (e.g. pig liver flavor, yeast), optionally at least one glidant (e.g. colloidal silicone dioxide), b) wet granulating the blend obtained in step a) with at least one binder (such as copovidone or povidone) and water, c) drying the granules and optionally milling, d) mixing the dried granules obtained in step c) with the second part of the disintegrant (e.g. croscarmellose), e) mixing at least one lubricant (e.g. stearic acid), and at least one glidant (e.g. anhydrous colloidal silica) to the granules obtained in step d), and f) optionally compressing the mixture obtained in step d) to form a tablet.

Step f) is omitted if the solid formulation is a granule. If the solid formulation is a tablet, step f) is carried out.

The invention preferably also relates to a solid formulation according to the invention, wherein the solid formulation is produced by a wet granulation process comprising or consisting of the steps: a)-e), and optionally step f), as defined in the present description.

The invention preferably relates to a granule formulation as obtained by the process above that can either be administered in the granular form or as tablets after compressing the final granules to tablets. Therefore, the solid formulation according to the invention preferably is a granule (or a plurality of such granules) or a tablet. The administration of the granules can take place by mixing with food or by offering the granules directly to the animal, e.g. in a bowl. The application of the granular form will allow an individual dosing of pimobendan according to the body weight of the animal.

The tablets according to the invention have additional advantages. As already mentioned, with the composition and the use of excipients according to the invention, it is possible to decrease the mass and the size of the tablets which allows a better feeding and/or swallowing by small animals, such as dogs, improving thereby compliance of the treatment.

The dissolution profile is ensuring immediate release of pimobendan. By ensuring an immediate release profile of pimobendan, the amount of drug to be administered can be kept as low as possible, thereby improving the safety profile especially for long-term treatment.

Moreover, the dosing accuracy of the tablet is very satisfactory. This is due to the fact that in accordance with the manufacturing process according to this invention, an excellent uniformity of pimobendan content is achieved. Furthermore, as it is illustrated by the examples, the tablets can be broken into halves, thirds or quarters so that half, third or quarter the dose per tablet can be administered. Dosing accuracy and compliance of both the animal and the animal owner are thus assured. This is of particular importance since pimobendan is usually administered for a life-long treatment.

Also, the palatability of the tablet is excellent. More than 90% of the dogs to whom the tablet according to this invention is given, accept the tablet voluntarily with only the tablet offered in a bowl. Compared with the existing gelatine capsule, the compliance of both the animal and the animal owner are significantly improved. This is even more important since the drug is administered for a life-long treatment.

The invention preferably also relates to a tablet according to the invention, wherein the tablet is stable for at least 18 months at 25° C. and 60% relative humidity.

Suitable packaging materials for tablets according to the invention are selected from, but not limited to: aluminum/aluminum blisters, PVC/PVDC blisters, and HDPE (high density polyethylene bottles).

The invention preferably also relates to a tablet according to the invention, wherein the tablet is round in shape. For such a tablet, characteristics like crushing strength, disintegration, uniformity of weight and content uniformity fulfill the requirements of the European Pharmacopoeia (ISBN/ISSN 92-871-5106-7 of 4th Edition 2004, Vol. 4.8, European Directorate for the Quality of Medicines (EDQM), European Pharmacopoeia, 226 Avenue de Colmar, F-67029 Strasbourg, France, http://www.pheur.org) and the United States Pharmacopoeia (http://www.usp.org: in print: USP-NF, catalog No. 2270001).

The invention preferably relates to a solid formulation, and most preferred a tablet according to the invention, wherein the solid formulation or tablet comprising 0.5-20 mg pimobendan, preferably of 1.25 mg, 2.5 mg, 5 mg or 10 mg pimobendan, and further comprises, preferably consists of, lactose (e.g. 25-45% by weight relative to the dry mass of the solid formulation/tablet=(w/w)), corn starch (e.g. 5-20% w/w), microcrystalline cellulose (e.g. 5-20% w/w), croscarmellose sodium (e.g. 3-8%), malic acid (e.g. 2.5-10% w/w), artificial beef flavor or pork liver flavor (e.g. 5-30% w/w), yeast (e.g. 4-20% w/w, preferably 6-10% w/w), copovidone (e.g. 2-8% w/w), colloidal anhydrous silica (e.g. 0.1-1, preferably 0.1-0.5% w/w), and stearic acid (e.g. 0.5-2.5% w/w), wherein the percentage by weight of pimobendan contains preferably about 0.333% (w/w) and the sum of the percentages by weight of all ingredients of the solid formulation including pimobendan is 100% (w/w). According to preferred embodiment, a solid formulation, and most preferred a tablet according to the invention, comprises 0.333% (w/w) pimobendan, 12.25% (w/w) corn starch, 6.2% (w/w) croscarmellose-sodium, 6.667% (w/w) malic acid, 12% (w/w) pork liver flavor, 8% (w/w) yeast, 5% (w/w) copovidone, 0.25% (w/w) colloidal anhydrous silica, 1.5% (w/w) stearic acid, 33.5% (w/w) lactose, and 14.3% (w/w) microcrystalline cellulose. Moreover, the skilled man also knows, that if he decided to reduce the amount of the pork liver flavor and yeast, for example, to the minimum of 5% (w/w), he can increase the amount of lactose, for example, to 48, 5% (w/w). The invention also relates to a solid formulation, preferably a tablet, comprising about 0.333% (w/w) pimobendan and any of the above other ingredients of the solid formulation, preferably the tablet, in the range given above so that the sum of the amounts by weight of the individual formulation ingredients is 100%.

The present invention is also directed to a solid formulation, preferably to a tablet, which comprises, preferably consists of 10 mg pimobendan, 800-1500 mg lactose, 300-400 mg corn starch, 40-200 mg croscarmellose-sodium, 100-300 mg malic acid anhydrous, 400-500 mg microcrystalline cellulose, 250-500 mg pork liver flavor, 150-350 mg yeast, 80-200 mg copovidone, 4-20 mg colloidal anhydrous silica, and 15-60 mg stearic acid for each 3000 mg of total weight of the solid formulation, preferably a tablet.

According to a further embodiment of the present invention, the solid formulation, preferably the tablet, comprises, preferably consists of 10 mg pimobendan, 900-1100 mg lactose, 340-380 mg corn starch, 150-190 mg croscarmellose-sodium, 150-250 mg malic acid anhydrous, 410-450 mg microcrystalline cellulose, 300-400 mg pork liver flavor, 200-300 mg yeast, 130-170 mg copovidone, 5-10 mg colloidal anhydrous silica, and 40-50 mg stearic acid for each 3000 mg of total weight of the solid formulation/tablet.

For example, the present invention relates to a solid formulation comprising for each 3000 mg of total weight: 10 mg pimobendan, 200 mg malic acid anhydrous, 1005 mg lactose, 367.5 mg corn starch, 150 mg copovidone, 186 mg croscarmellose sodium, 429 mg microcrystalline cellulose, 360 mg pork liver flavor, 240 mg yeast, 45 mg stearic acid, and 7.5 mg colloidal anhydrous silica. A skilled man is in a position to prepare such solid formulation/tablet. The skilled man also knows that the amount of each ingredient of the solid formulation/tablet can vary within the percentages given above in that the total weight of the solid formulation/tablet for each 0.333 mg pimobendan is 100 mg.

In another important embodiment, the invention relates to a wet granulation process comprising, preferably consisting of the steps:

a) mixing pimobendan or a pharmaceutically acceptable salt thereof or crystalline forms thereof, a first part of disintegrant (e.g. croscarmellose), malic acid, at least one diluent (such as starch, lactose and/or cellulose derivatives), a flavoring agent (e.g. pig liver flavor, yeast), optionally at least one glidant (e.g. colloidal silicone dioxide), b) wet granulating the blend obtained in step a) with at least one binder (such as copovidone or povidone) and water, c) drying the granules and optionally milling, d) mixing the dried granules obtained in step c) with the second part of the disintegrant (e.g. croscarmellose), e) mixing at least one lubricant (e.g. stearic acid), and at least one glidant (e.g. anhydrous colloidal silica) to the granules obtained in step d), and f) optionally compressing the mixture obtained in step d) to form a tablet.

Step f) is omitted if the solid formulation is a granule. If the solid formulation is a tablet, step f) is carried out.

Said process allows preparing a solid formulation according to the invention. The amounts of compounds identified above in the process of the invention are introduced in such a way that the amounts thereof in the prepared solid formulation are as described above, including the specific or preferred embodiments.

Another embodiment is a method of prevention and/or treatment of diseases wherein cardiotonic, hypotensive and anti-thrombotic substances have a therapeutic benefit, comprising administering to a mammal in need of such treatment a therapeutically effective amount of a solid formulation according to the invention as disclosed above, including the specific or preferred embodiments.

Preferred is a method of prevention and/or treatment of congestive heart failure, comprising administering to a mammal in need of such treatment a therapeutically effective amount of a solid formulation according to the invention as disclosed above. Most preferably, the method comprises administering a tablet according to the invention, wherein the tablet comprises, preferably consists of 1.25 mg, 2.5 mg, 5 mg or 10 mg pimobendan, and further comprises, preferably consists of lactose, corn starch, croscarmellose sodium, microcrystalline cellulose, malic acid, preferably at an amount of 100 mg/1.5 g of the tablet, pork liver flavor, yeast, copovidone, colloidal anhydrous silica and stearic acid.

Preferably also, such treatment is by orally applying the solid formulation according to the invention.

The mammal according to the invention is preferably a small animal. Said small animal is preferably selected from the group consisting of dogs, cats and rodents, such as rabbits.

Furthermore, the invention relates to a method for manufacturing a medicament for the prevention and/or treatment of congestive heart failure, wherein a solid formulation according to the invention is used. Preferably, the invention relates to a method for manufacturing a medicament for the prevention and/or treatment of congestive heart failure, wherein a tablet consisting of 1.25 mg, 2.5 mg, 5 mg or 10 mg pimobendan and further consisting of lactose, corn starch, croscarmellose sodium, microcrystalline cellulose, 100 mg malic acid for 1.5 g of the tablet, pork liver flavor, yeast, copovidone, colloidal anhydrous silica and stearic acid is used.

The present invention furthermore relates to a kit, comprises a solid formulation, preferably a tablet according to the present invention described herein, and a package leaflet or user instruction including the information that the solid formulation, preferably the tablet is to used, preferably via the oral route for the prevention and/or treatment of congestive heart failure in a mammal in need of such prevention or treatment, preferably in a small animal, such as dog, cat or rodent.

The following examples serve to further illustrate the present invention; but the same should not be construed as limiting the scope of the invention disclosed herein.

EXAMPLES

Example 1

Composition of tablets according to the present invention with malic acid (C752) is given hereafter with a comparison to the Vetmedin® formulation (according to EP 1725218 B1)

The tablets according to the invention as described in table 1 were made as shown in the manufacturing process depicted in FIG. 1.

Example 2: Dissolution Profiles

Comparison of the dissolution profiles of Pimobendan in Vetmedin® tablets (containing citric acid) and tablets of the invention (containing malic acid).
Study Conditions:
  Rotation speed: 75 rpm
  Temperature: 37° C.
  Media: HCl 0.1 N—Citrate buffer ph 4.0—Phosphate buffer pH 6.8

Figure 2:
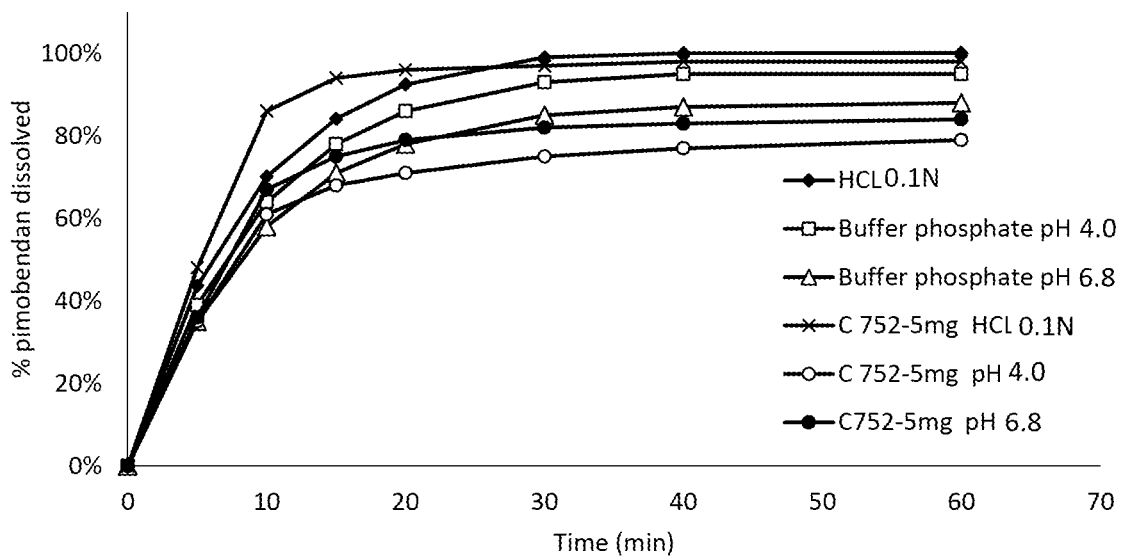
FIG. 2: Dissolution Profiles—Comparison of Pimobendan 5 mg tablets sold under the name Vetmedin® 5 mg chewable tablets for dogs, by Boehringer Ingelheim (with citric acid), with Pimobendan 5 mg tablets according to the invention (with malic acid) (C752) in several media: HCl 0.1 N; phosphate buffer pH4.0, and phosphate buffer pH6.8, RSD <5% after 5 min., USP apparatus 2 (Paddle), Rotation Speed 75 rpm, Temperature 37° C. ━●━ HCL 0.1 N ━□━ Buffer phosphate pH 4.0 ━▲━ Buffer phosphate pH 6.8 ━✳━ C 752-5 mg HCL0.1N ━○━ C 752-5 mg pH 4.0 ━●━ C752-5 mg pH 6.8

Examples for representative dissolution profiles of the 5 mg tablets according to this invention (C752) and compared with tablets of Vetmedin® 5 mg are as disclosed in FIG. 2.

Dissolution profiles, pimobendan 5 mg tablets showing 95% confidence intervals of the mean usp apparatus 2 (paddle), rotation speed 75 rpm,

Example 3

Change in the Size and Mass of the Tablets

With the composition of the tablets of the invention and the use of the excipients described in the present invention, it is possible to decrease the mass and the size of the tablets which allows a better palatability and therefore treatment compliance for the dogs.

Tablet Mass Comparison

TABLE 2

| Tablets Pimobendan content | 1.25 mg | 5 mg | 10 mg |
|---|---|---|---|
| Vetmedin ® mg | 500 | 2000 | 4000 |
| Present formulation (C752) mg | 375 | 1500 | 3000 |

TABLE 1

| | Vetmedin ® 1.25-2.5-5 mg According to EP1725218 B1) | | | | C752 1.25-5-10 mg According to the invention | | | |
|---|---|---|---|---|---|---|---|---|
| Ingredients | Content (wt. %) | mg/ tablet | mg/ tablet | mg/ tablet | Content (wt. %) | mg/ tablet | mg/ tablet | mg/ tablet |
| Pimobendan | 0.25 | 1.25 | 2.5 | 5 | 0.333 | 1.25 | 5 | 10 |
| citric acid | 5 | 25 | 50 | 100 | | | | |
| malic acid | | | | | 6,667 | 25 | 100 | 200 |
| corn starch | 32.625 | 163.125 | 326.25 | 652.5 | 12.25 | 45.94 | 183.75 | 367.5 |
| Lactose | 32.625 | 163.125 | 326.25 | 652.5 | 33.5 | 125.63 | 502.5 | 1005 |
| microcrystalline cellulose | | | | | 14.3 | 53.63 | 214.5 | 429 |
| povidone | 4 | 20 | 40 | 80 | | | | |
| Copovidone | | | | | 5 | 18.75 | 75 | 150 |
| croscarmellose Na | 4 | 20 | 40 | 80 | 6.2 | 23.25 | 93 | 186 |
| artificial beef flavour | 20 | 100 | 200 | 400 | | | | |
| pork liver flavor | | | | | 12 | 45 | 180 | 360 |
| Yeast | | | | | 8 | 30 | 120 | 240 |
| Silica colloidal anhydrous | 0.5 | 2.5 | 5 | 10 | 0.25 | 0.94 | 3.75 | 7.5 |
| Magnesium stearate | 1 | 5 | 10 | 20 | | | | |
| stearic acid | | | | | 1.5 | 5.63 | 22.5 | 45 |
| Total | 100.0 | 500.0 | 1,000.0 | 2,000.0 | 100.0 | 375.0 | 1,500.0 | 3,000.0 |

Tablet Size Comparison

TABLE 3

| Tablets Pimobendan content | 1.25 mg | 5 mg | 10 mg |
|---|---|---|---|
| Vetmedin ® mm (oval tablets) | 19/7 | 25/15 | 28/19 |
| Present formulation (C752) mm (round tablets) | 10 | 18 | 22.6 |

Example 4

Comparison of three batches of tablets comprising 1.25 mg of pimobendan:
E 70: formula with succinic acid (comparative formula))
E 74: formula with malic acid (according to the invention)
E 77: formula with malic acid/composition C 752 (according to the invention)
The formulas are the following:

TABLE 4

| | 1.25 mg Pimobendan | | |
|---|---|---|---|
| Batches | E 70 | E 74 | E 77 |
| Pimobendan batch | 0.333% | 0.333% | 0.333% |
| Malic acid powder | | 6.667% | 6.667% |
| Succinic acid | 6.667% | | |
| Corn starch Q S | 12.36% | 12.36% | 12.24% |
| Lactose monohydrate | 33.00% | 33.00% | 33.64% |
| Croscarmellose sodium | 6.25% | 6.25% | 5.20% |
| Cellulose microcrystalline | 15.50% | 15.50% | 14.31% |
| Pig liver powder | 12.00% | 12.00% | 12.00% |
| Yeast | 8.00% | 8.00% | 8.00% |
| Povidone K 29/32 | 4.14% | 4.14% | |
| Copovidone | | | 5.07% |
| total: | 98.25% | 98.25% | 97.25% |
| Croscarmellose sodium | | | 1.00% |
| Stearic acid | 1.50% | 1.50% | 1.50% |
| Silica colloidal anhydrous | 0.25% | 0.25% | 0.25% |
| total: | 100.00% | 100.00% | 100.00% |

The three batches of tablets as detailed above in table 4 were prepared as shown in the manufacturing process depicted in FIG. 1.

Dissolution Profiles

Comparison of the dissolution profiles of Pimobendan in Vetmedin® tablets (containing citric acid), tablets with succinic acid (E70, Table 5) and tablets of the invention containing malic acid (E74 and E77, Table 5) was made.

The study conditions were the same as in Example 2.

Figure 3:
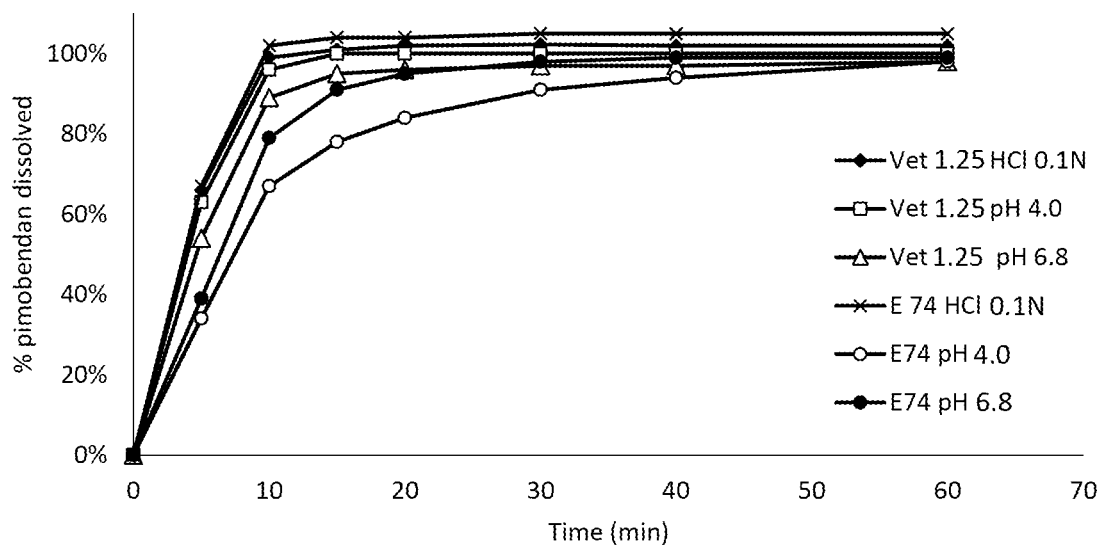
FIG. 3: Dissolution profiles of 1.25 mg tablets according to the invention (E74, Table 5) and tablets of Vetmedin® 1.25 mg ━●━ Vet 1.25 HCl 0.1N ━□━ Vet 1.25 pH 4.0 ━△━ Vet 1.25 pH 6.8 ━✳━ E 74 HCl 0.1 N ━○━ E74 pH 4.0 ━●━ E74 pH 6.8

The dissolution profiles of the 1.25 mg tablets according to the invention (E74, Table 5) and tablets of Vetmedin® 1.25 mg are shown in FIG. 3.

Figure 4:
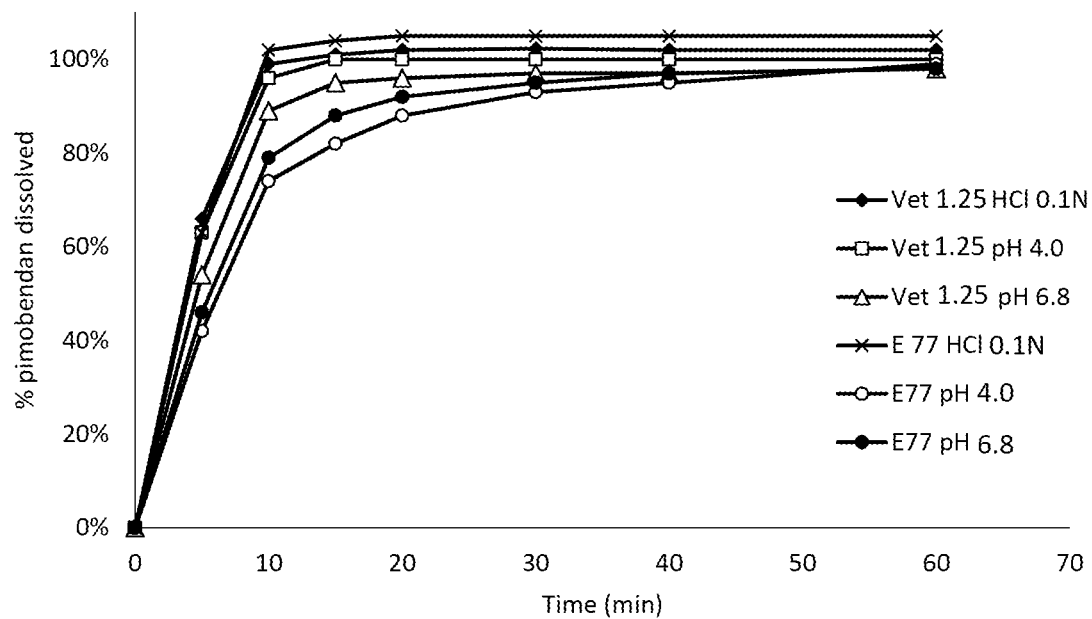
FIG. 4: Dissolution profiles of 1.25 mg tablets according to the invention (E77, Table 5) and tablets of Vetmedin® 1.25 mg ━●━ Vet 1.25 HCl 0.1N ━□━ Vet 1.25 pH 4.0 ━△━ Vet 1.25 pH 6.8 ━✶━ E 77 HCl 0.1 N ━○━ E77 pH 4.0 ━●━ E77 pH 6.8

The dissolution profiles of the 1.25 mg tablets according to the invention (E77, Table 5) and tablets of Vetmedin® 1.25 mg are shown in FIG. 4.

Figure 5:
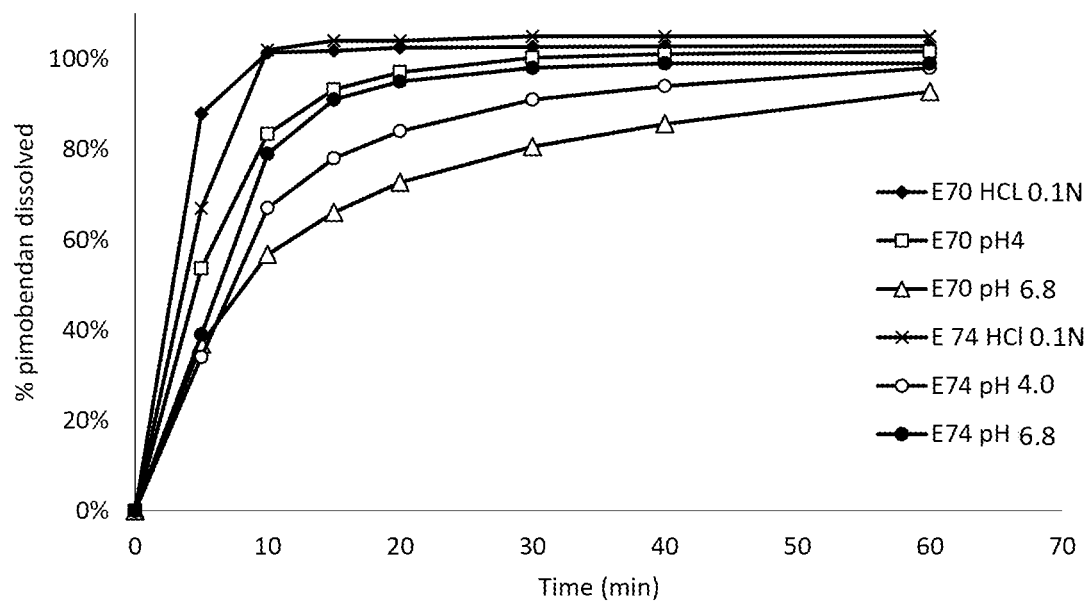
FIG. 5: Dissolution profiles of 1.25 mg tablets with succinic acid (E70, Table 5) and 1.25 mg tablets according to the invention (E74, Table 5) ━✦━ E70 HCL 0.1N ━○━ E70 pH4 ━●━ E70 pH6.8 ━✶━ E 74 HCl 0.1 N ━○━ E74 pH 4.0 ━●━ E74 pH 6.8

The dissolution profiles of the 1.25 mg tablets with succinic acid (E70, Table 5) and 1.25 mg tablets according to the invention (E74, Table 5) are shown in FIG. 5.

Figure 6:
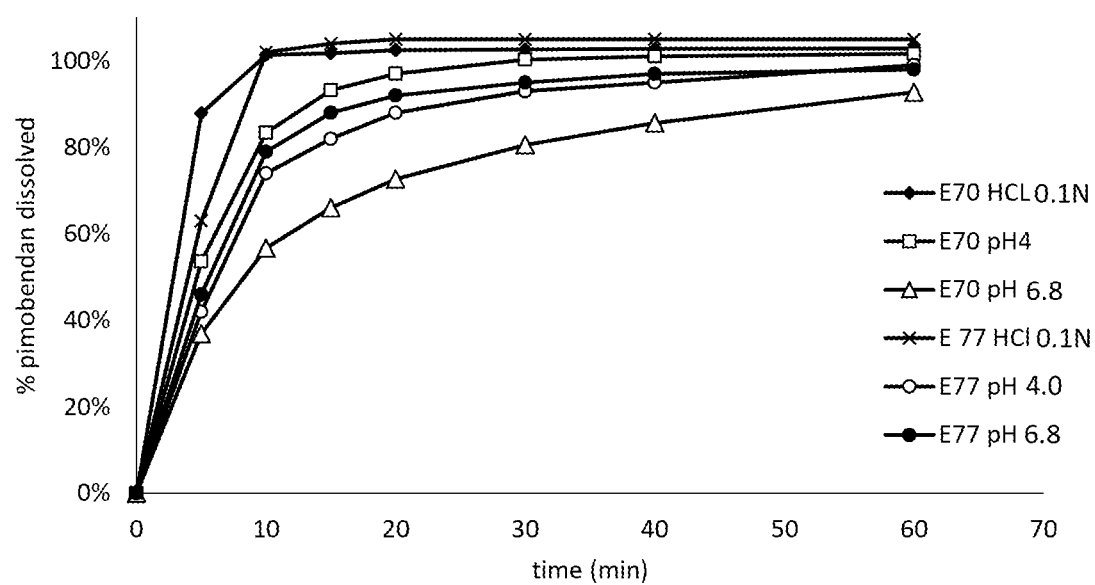
FIG. 6: Dissolution profiles of 1.25 mg tablets with succinic acid (E70, Table 5) and 1.25 mg tablets according to the invention (E77, Table 5) ━✦━ E70 HCL 0.1N ━○━ E70 pH4 ━●━ E70 pH6.8 ━✶━ E 77 HCl 0.1N ━○━ E77 pH 4.0 ━●━ E77 pH 6.8

The dissolution profiles of the 1.25 mg tablets with succinic acid (E70, Table 5) and 1.25 mg tablets according to the invention (E77, Table 5) are shown in FIG. 6.

Tablets with succinic acid show more differences in dissolution of Pimobendan between pHs than malic acid tablets.

Tablet Hardness Comparison

TABLE 5

| Batches | E 70 (succinic ac.) | E 74 (malic ac.) | E 77 (malic ac.) |
|---|---|---|---|
| hardness (kp) | 5.7 | 6.6 | 6.6 |
| thickness (mm) | 4.5 | 4.5 | 4.5 |

With identical thickness, hardness of tablets according to the invention is higher than tablets with succinic acid.

Maximal Obtainable Hardness

TABLE 6

| Batches | E 70 (succinic ac.) | E 74 (malic ac.) | E 77 (malic ac.) |
|---|---|---|---|
| hardness max (kp) | 5.7 | 7.5 | 9.3 |

Maximal hardness of tablets according to the invention is higher than tablets with succinic acid which in turn results in less damaged tablets during tablet processing and packaging.

Example 5

Process Simplification and Tablets Properties Improvement

The process described in EP 1725218 B1 patent is based on the following: Pimobendan is dispersed in the granulation solvent (aqueous binder solution) and is then sprayed onto the raw materials blend using a Fluid Air Bed equipment.

The manufacture of the tablets of the invention is based on a wet granulation process without spraying of pimobendan onto the excipients blend. The active ingredient is directly blended with the others excipients, and then granulated with a copovidone solution.

The solution provided here allows obtaining an accurate dosage of granulation (and therefore accurate dosage of tablets) with an easy process.

Tablets Properties Improvement

Accuracy of dosage regimen is one of the key factors for a successful treatment. With the improvement of tablets properties and design, it is possible to increase the accuracy of the administered dose.

Therefore, tablets A and C752, both according to the invention, have been designed here in a four-scored shape with an improvement in terms of hardness, breakability and friability.

The improvements considered are the following:

The use of stearic acid instead of magnesium stearate increases the hardness and decreases the friability of the tablet.

By adding cellulose, hardness and friability are equivalent, but during the manufacturing, the compression force applied by the tablet press is lower for the same tablet hardness.

TABLE 7

| Tablets (invention) | Tablet A | C752 |
|---|---|---|
| Starch | 28% | 12% |
| Microcrystalline cellulose | 0% | 14.3% |
| Magnesium stearate | 0% | 0% |
| Stearic acid | 1.50% | 1.50% |
| Hardness N | 61 | 60 |
| Friability | <1% | <1% |
| Splitability ½ tb | complies | complies |

Components and contents thereof not specified in table 7 are the same as in table 1.

Comparison between target hardness for Vetmedin® tablets (reference: U.S. Pat. No. 8,846,680 or measurement) and tablets of the invention.

Tablet hardness comparison

TABLE 8

| Tablets Pimobendan content | 1.25 mg | 5 mg | 10 mg |
|---|---|---|---|
| Vetmedin ® hardness N | 140 | 190 | 350 |
| C752 hardness N | 30 to 80 | 50 to 140 | 90 to 160 |

Table 8 shows that use of Copovidone (Kollidon® VA 64) as binder agent in the granulating solution improves the resistance of the tablets:

This is confirmed by the results of the friability test even at very low hardness for the three sizes of tablets. All the results are lower than the friability specification 1%).

Tablet friability at low hardness

TABLE 9

| C752 Batch Number | 1 | 2 | 3 |
|---|---|---|---|
| Pimobendan mg | 1.25 | 5 | 10 |
| Tablet weight mg | 375 | 1500 | 3000 |
| Hardness N | 30 | 50 | 90 |
| Tablet | 1 | 1 | 1 |
| Friability % | 0.83 | 0.74 | 0.55 |

The shape and the score of the tablets allow breaking the tablet of the invention 1.25 mg in two halves and the tablets 5 and 10 mg in two halves or four quarters. For each split portion, the friability is low.

Tablet and splits portions friability at target hardness

TABLE 10

| | C752 Batch number | | | | | | | |
|---|---|---|---|---|---|---|---|---|
| | 1 | | 2 | | | 3 | | |
| Pimobendan mg | 1.25 | | 5 | | | 10 | | |
| Hardness N | 60 | | 95 | | | 120 | | |
| Tablet | 1 | ½ | 1 | ½ | ¼ | 1 | ½ | ¼ |
| weight mg | 375 | 187.5 | 1500 | 750 | 375 | 3000 | 1500 | 750 |
| Friability % | 0.22 | 0.6 | 0.23 | 0.35 | 0.72 | 0.25 | 0.56 | 0.88 |

The Pimobendan content uniformity (CU) is measured on half tablets for the 1.25 mg tablets and on the quarter tablet for the 5 and 10 mg tablets. 10 tablets portions of two different batches are analyzed for each tablets size.

1.25 mg tablets of the invention (C752)—Content uniformity for ½ tablets

TABLE 11

| | C752 Batch number | | | |
|---|---|---|---|---|
| | 1 | | 4 | |
| Tablet | Individual content mg/½ tab | recovery % | Individual content mg/½ tab | recovery % |
| 1 | 0.617 | 98.72 | 0.616 | 98.56 |
| 2 | 0.596 | 95.36 | 0.584 | 93.44 |
| 3 | 0.605 | 96.8 | 0.622 | 99.52 |
| 4 | 0.563 | 90.08 | 0.636 | 101.76 |
| 5 | 0.629 | 100.64 | 0.680 | 108.8 |
| 6 | 0.614 | 98.24 | 0.663 | 106.08 |
| 7 | 0.63 | 100.8 | 0.663 | 106.08 |
| 8 | 0.666 | 106.56 | 0.582 | 93.12 |
| 9 | 0.62 | 99.2 | 0.619 | 99.04 |
| 10 | 0.655 | 104.8 | 0.634 | 101.44 |
| Means: | 0.620 | 99.12 | 0.630 | 100.78 |

TABLE 12

| | | C752 Batch number | |
|---|---|---|---|
| | specifications | 1 | 4 |
| CU Min | >0.531 | 0.563 | 0.582 |
| CU Max | <0.718 | 0.666 | 0.663 |
| CU average | 0.594-0.656 | 0.62 | 0.63 |

Pimobendan theoretical value for ½ tablet: 0.625 mg 1.5 mg tablets of the invention (C752)—Content uniformity for ¼ tablets—theorical value

TABLE 13

| | | C752 Batch number | |
|---|---|---|---|
| | specificatons | 2 | 5 |
| CU Min | >1.06 | 1.14 | 1.21 |
| CU Max | <1.44 | 1.32 | 1.41 |
| CU average | 1.19-1.31 | 1.24 | 1.28 |

2.5 mg tablets of the invention (C752)—Content uniformity for ¼ tablets—theorical value

TABLE 14

| | specifications | C752 Batch number | |
| --- | --- | --- | --- |
| | | 3 | 6 |
| CU Min | >2.12 | 2.25 | 2.4 |
| CU Max | <2.87 | 2.66 | 2.74 |
| CU average | 2.37-2.63 | 2.46 | 2.54 |

5 mg tablets of the invention (C752)—Content uniformity for ¼ tablets

TABLE 15

| | C752 Batch number | | | |
| --- | --- | --- | --- | --- |
| | 2 | | 5 | |
| Tablets | Individual content mg/¼ tab | recovery % | Individual content mg/¼ tab | recovery % |
| 1 | 1.14 | 91.28 | 1.30 | 104.32 |
| 2 | 1.31 | 104.4 | 1.32 | 105.76 |
| 3 | 1.25 | 100.32 | 1.41 | 112.48 |
| 4 | 1.19 | 95.04 | 1.29 | 102.96 |
| 5 | 1.29 | 102.88 | 1.25 | 99.84 |
| 6 | 1.24 | 98.96 | 1.27 | 101.28 |
| 7 | 1.23 | 98.64 | 1.22 | 97.92 |
| 8 | 1.22 | 97.28 | 1.22 | 97.84 |
| 9 | 1.32 | 105.52 | 1.21 | 97.12 |
| 10 | 1.21 | 96.4 | 1.30 | 103.6 |
| Means: | 1.24 | 99.07 | 1.28 | 102.31 |

10 mg tablets of the invention (C752)—Content uniformity for ¼ tablets

TABLE 16

| | C752 Batch number | | | |
| --- | --- | --- | --- | --- |
| | 3 | | 6 | |
| Tablets | Individual content mg/¼ tab | recovery % | Individual content mg/¼ tab | recovery % |
| 1 | 2.28 | 91.32 | 2.58 | 103.28 |
| 2 | 2.43 | 97.36 | 2.54 | 101.6 |
| 3 | 2.66 | 106.44 | 2.62 | 104.96 |
| 4 | 2.42 | 96.92 | 2.50 | 100.04 |
| 5 | 2.25 | 90.12 | 2.53 | 101.2 |
| 6 | 2.55 | 101.92 | 2.45 | 98.12 |
| 7 | 2.43 | 97.32 | 2.40 | 96.12 |
| 8 | 2.54 | 101.4 | 2.74 | 109.44 |
| 9 | 2.56 | 102.56 | 2.50 | 100.12 |
| 10 | 2.50 | 100.08 | 2.57 | 102.76 |
| Means : | 2.46 | 98.54 | 2.54 | 101.76 |

For the three tablets of the invention (Pimobendan 1.25-5-10 mg), content uniformity is within the defined specifications for all parts of tablets.

CONCLUSIONS

Development of the tablets of the invention allows to demonstrate the following points:

The substitution of citric acid by malic acid allows dissolving Pimobendan in the same conditions.

It renders possible to manufacture tablets with a simpler process while having an improved ratio of compliant tablets.

Mass and shape of the tablets and accuracy of the dose can further be improved for a better treatment of the dogs;

Moreover, replacing succinic acid by malic acid leads to an improved production yield because of the higher hardness of the tablets, and to a better dissolution profile in neutral pH (pH6.8).

The invention claimed is:

1. A solid formulation, comprising pimobendan or a pharmaceutically acceptable salt thereof which is dispersed in malic acid, wherein the solid formulation further comprises copovidone, microcrystalline cellulose, and stearic acid, wherein a weight ratio of pimobendan or a pharmaceutically acceptable salt thereof to malic acid ranges from 1:10 to 1:40, and wherein stearic acid is 1.5% (w/w) 2.5% (w/w) of the solid formulation, wherein pimobendan or a pharmaceutically acceptable salt thereof is the only active agent and the formulation comprises 0.5 to 20 mg of pimobendan or a pharmaceutically acceptable salt thereof.

2. The solid formulation according to claim 1, further comprising pharmaceutically acceptable carriers and/or excipients.

3. The solid formulation according to claim 1, further comprising pharmaceutically acceptable carriers selected from the group consisting of starch and lactose.

4. The solid formulation according to claim 1, further comprising starch, wherein the starch is corn starch.

5. The solid formulation according to claim 1, comprising a dose selected from the group consisting of 1.25 mg, 2.5 mg, 5 mg and 10 mg of pimobendan.

6. The solid formulation according to claim 1, wherein the weight of the whole solid formulation is in the range of 250 to 3000 mg.

7. The solid formulation according to claim 1, wherein the solid formulation comprises 1.25 mg, 2.5 mg, 5 mg or 10 mg pimobendan, and further comprises lactose, corn starch, croscarmellose sodium, microcrystalline cellulose, malic acid, at an amount of 100 mg/1.5 g of the solid formulation, pork liver flavor, yeast, copovidone, colloidal anhydrous silica and stearic acid.

8. The solid formulation according to claim 1, wherein the solid formulation is a tablet or granules.

9. A method for the treatment of congestive heart failure, the method comprising administering to a mammal in need thereof a therapeutically effective amount of the solid formulation according to claim 1.

10. A kit comprising the solid formulation according to claim 1 and a package leaflet or user instruction including the information that said formulation is to use for treatment of congestive heart failure in a mammal in need of such treatment.

* * * * *